United States Patent [19]

Lang et al.

[11] 4,228,151

[45] Oct. 14, 1980

[54] COSMETIC COMPOSITION FOR IMPARTING TO HUMAN SKIN A COLORATION RESEMBLING A NATURAL TAN

[75] Inventors: Gérard Lang, Epinay-sur-Seine; Serge Forestier, Claye-Souilly, both of France

[73] Assignee: L'Oreal, Paris, France

[21] Appl. No.: 793,317

[22] Filed: May 3, 1977

[30] Foreign Application Priority Data

May 3, 1976 [FR] France ................................ 76 13165

[51] Int. Cl.[3] .......................... A61K 7/42; A61K 7/44; A61K 7/021; A61K 31/495

[52] U.S. Cl. ........................................ 424/60; 424/47; 424/59; 424/63; 424/250

[58] Field of Search ..................... 424/250, 47, 60, 63, 424/59; 260/250 QN

[56] References Cited

U.S. PATENT DOCUMENTS

| | | | |
|---|---|---|---|
| 2,626,259 | 1/1953 | Landquist et al. | 260/250 QN |
| 2,880,140 | 3/1959 | de Navarve | 424/60 |
| 3,065,144 | 11/1962 | Kreps | 424/60 |
| 3,250,681 | 5/1966 | Zbornik et al. | 424/60 |
| 3,344,022 | 9/1967 | Johnston | 260/250 QN |
| 3,814,756 | 6/1974 | Seng et al. | 260/250 QN |
| 3,862,951 | 1/1975 | Gottwald et al. | 260/289 R |
| 3,991,053 | 11/1976 | Czuba et al. | 260/250 QN |
| 4,022,777 | 5/1977 | Sam et al. | 260/250 QN |

FOREIGN PATENT DOCUMENTS

| | | |
|---|---|---|
| 1288282 | 2/1962 | France . |
| 1494068 | 9/1967 | France . |
| 2151103 | 4/1977 | France . |
| 1121104 | 7/1968 | United Kingdom . |
| 1140298 | 1/1969 | United Kingdom . |
| 1186619 | 4/1970 | United Kingdom . |
| 1201057 | 8/1970 | United Kingdom . |
| 1252937 | 11/1971 | United Kingdom . |
| 1308370 | 2/1973 | United Kingdom . |
| 1315524 | 5/1973 | United Kingdom . |
| 1324629 | 7/1973 | United Kingdom . |
| 1365441 | 9/1974 | United Kingdom . |
| 1374360 | 11/1974 | United Kingdom . |
| 1377306 | 12/1974 | United Kingdom . |
| 1432443 | 4/1976 | United Kingdom . |

*Primary Examiner*—Allen J. Robinson
*Attorney, Agent, or Firm*—Cushman, Darby & Cushman

[57] ABSTRACT

A cosmetic composition for imparting to human skin after exposure to sunlight a coloration resembling a natural tan comprises a cosmetic vehicle suitable for topical application to the skin and an effective amount of at least one compound of the formula

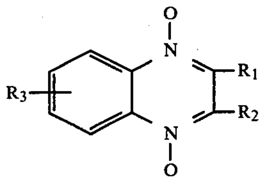

wherein $R_1$ and $R_2$ each independently represent hydrogen, an aliphatic radical having 1–18 carbon atoms, carbalkoxy having 2–5 carbon atoms, acyl having 2–5 carbon atoms, aryl, aryl substituted by alkyl having 1–4 carbon atoms or hydroxy, a heterocycle containing 4–6 members, substituted or not by alkyl having 1–4 carbon atoms, halogen or hydroxy, or $R_1$ and $R_2$ together form a saturated ring containing 4–12 chains, optionally substituted by alkyl having 1–4 carbon atoms, halogen or hydroxy, or bridged and containing a heteroatom selected from N, O or S; and $R_3$ represents hydrogen, a lower aliphatic group containing 1–6 carbon atoms, lower alkoxy containing 1–4 carbon atoms or halogen, with the proviso that $R_1$, $R_2$ and $R_3$ are not hydrogen simultaneously; and an acid addition salt thereof.

19 Claims, No Drawings

COSMETIC COMPOSITION FOR IMPARTING TO HUMAN SKIN A COLORATION RESEMBLING A NATURAL TAN

The present invention relates to a new cosmetic composition for imparting to human skin, a coloration essentially comparable to a natural tan.

As is known, natural tanning of human skin is due to melanization resulting from exposure of the skin to light rays having a wave length between 280 and 400 millimicrons. However, this exposure which is necessary to obtain a tan appearance of the skin very often, and especially when the exposure is for a long period of time, can cause not only very painful burns but also for those with sensitive skin, long term skin problems, and for many, very unesthetic peeling of the skin.

To avoid these disadvantages, it is possible to apply to the skin compositions containing a more or less selective solar filter. However, if these compositions are successful in avoiding solar burns, they generally also retard, by reason by their very nature, the production of the desired tan appearance. This often prompts persons who desire a rapid tanning not to use these compositions, thereby risking encountering the above mentioned disadvantages.

Heretofore, it has also been proposed to use compositions for imparting to the skin an artificial tan appearance. A particular composition of this type is one which is based on dihydroxy acetone, disclosed, for instance, in French Pat. No. 1,250,185. The tan obtained through the use of dihydroxy acetone results from a reaction between the active product and the protein components of the skin, independently of an exposure to the sun.

The use of such compositions, however, has several drawbacks in achieving an artificial tan which resembles as much as possible a natural tan.

In effect, because of the mechanism at the outset, very often after successive applications, different shades result depending on the amount of callous skin treated. Further, the coloration obtained in irregularly removed by washing which also leads to undesired shade variations.

Moreover, the production of a skin coloration which is independent of exposure to sunlight accentuates for many the artificiality of the tan. Thus, even though many people may desired to get tanned rapidly, nonetheless they generally desire that the tanning be effected as naturally as possible, that is to say, by exposure to the sun.

It has now been found that by applying to the skin a composition containing at least one quinoxaline derivative a coloration essentially similar to a natural tan can be achieved in less time than is required to obtain a natural tan after exposure of the thus treated skin to ultra-violet rays having a wave length between 320 and 400 millimicrons.

It has also been found that this coloration does not result from a reaction of the active product with the protein components of the skin. The tan coloration achieved is uniform; it covers completely the areas of the skin exposed to the sun rays and it is resistant to water and soaping.

The compounds employed in the composition of the present invention also do not react with solar filters conventionally employed in this type of composition. Therefore, these compounds can be used in combination with these known solar filters, thus providing not only protection for the skin but also a rapid tanning of the skin.

It is therefore a principal object of the present invention to provide a cosmetic composition for imparting to human skin a coloration essentially identical to a natural tan, after exposure of the skin to radiation having a wave length between 320 and 400 millimicrons, said composition containing at least one quinoxaline derivative.

Another object of the present invention is the provision of a process for coloring the skin by the action of ultra-violet rays.

The composition according to the present invention comprises a cosmetic vehicle for topical application to the skin and an effective amount of at least one quinoxaline derivative of the formula

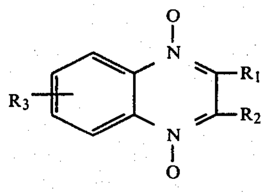

(I)

wherein $R_1$ and $R_2$ each independently represent hydrogen; an aliphatic radical having, preferably, 1–18 carbon atoms and particularly a linear or branched alkyl, and more particularly, methyl, ethyl, propyl, isopropyl, butyl, hexyl, decyl, and hexadecyl; carbalkoxy having, preferably, 2–5 carbon atoms, and particularly carbethoxy; acyl having, preferably 2–5 carbon atoms, such as acetyl; aryl such as, preferably, phenyl and phenyl substituted by one or more alkyl groups having 1–4 carbon atoms such as, preferably, methyl, ethyl or propyl, or hydroxy; a heterocycle having 4–6 members and preferably morpholino, piperidino, optionally substituted by alkyl having, preferably 1–4 carbon atoms such as methyl, ethyl, propyl, halogen such as bromine or chlorine, or hydroxy; $R_1$ and $R_2$ being able also to form together a saturated ring having 4–12 members, optionally substituted by alkyl having, preferably, 1–4 carbon atoms such as, preferably, methyl or ethyl, a halogen such as chlorine or bromine and hydroxy, or bridged and being able to contain a heteroatom such as N, O or S;

$R_3$ represents hydrogen; a lower aliphatic radical having, preferably, 1–6 carbon atoms such as lower alkyl and preferably methyl or ethyl; lower alkoxy having preferably 1–4 carbon atoms and more particularly methoxy or ethoxy, and halogen such as, preferably, chlorine or bromine;

with the proviso that $R_1$, $R_2$ and $R_3$ do not represent hydrogen simultaneously.

The more particularly preferred of the quinoxaline derivatives of formula I above are those wherein:

$R_1$ and $R_2$ each independently represent hydrogen; an aliphatic radical having 1–18 carbon atoms and in particular, linear or branched alkyl having 1–18 carbon atoms; carbalkoxy having 2–5 carbon atoms; acyl having 2–5 carbon atoms; phenyl or phenyl substituted by OH; or $R_1$ and $R_2$ form together a saturated ring containing 4–12 carbon atoms; $R_3$ represents hydrogen, alkoxy having 1–4 carbon atoms, halogen or alkyl having 1–4 carbon atoms.

Among these compounds, those quinoxaline derivatives of formula (I) which provide the most remarkable results are those wherein $R_1$ and $R_2$ each independently represent methyl, ethyl, isopropyl, decyl, hexadecyl, carbethoxy, acetyl, phenyl, phenyl substituted by OH or wherein $R_1$ and $R_2$ together form a propylene, butylene or decylene chain; and $R_3$ represents hydrogen, methoxy, methyl or chlorine.

Representative quinoxaline derivatives usefully employed in the present invention include:
3-methyl quinoxaline di-N-oxide,
2,3-dimethyl quinoxaline di-N-oxide,
2-ethyl-3-methyl quinoxaline di-N-oxide,
2,3-propylene quinoxaline di-N-oxide,
2,3-butylene quinoxaline di-N-oxide,
2-isopropyl-3-methyl quinoxaline di-N-oxide,
2-methyl-3-phenyl quinoxaline di-N-oxide,
2-methyl-3-p-hydroxyphenyl quinoxaline di-N-oxide,
2-decyl-3-methyl quinoxaline di-N-oxide,
2-hexadecyl-3-methyl quinoxaline di-N-oxide,
2,3-decylene quinoxaline di-N-oxide,
2-carbethoxy-3-methyl quinoxaline di-N-oxide,
2acetyl-3-methyl quinoxaline di-N-oxide,
2,3-dimethyl-6-methoxy quinoxaline di-N-oxide,
2,3-dimethyl-6-chloro quinoxaline di-N-oxide and
2-ethyl-3,6-dimethyl quinoxaline di-N-oxide.

The salts of addition with mineral or organic acids of the said quinoxaline derivative can also be employed. Preferably the addition salts are the hydrochloride, the sulfate, the acetate, the lactate, the perchlorate, the citrate and the stearate thereof.

The composition in accordance with the present invention can contain one or more quinoxaline derivatives defined above which is present in an amount between 0.5 and 10, and preferably between 2 and 5 percent by weight relative to the total weight of the composition. The amount of the quinoxaline derivative can vary depending on the nature of the derivative itself as well as the coloration desired; the more pronounced the color desired, generally a greater amount of quinoxaline derivative is used. The pH of the composition of the present invention is generally between 3 and 8.5 and preferably between 4 and 6.

The cosmetic composition of this invention should be provided in a form which can be uniformly spread on the skin so as to obtain even distribution of the quinoxaline derivative thereon. Thus, the composition can be provided in the form of a lotion, a gel or an emulsion, the preferred form being an emulsion having a continuous aqueous phase.

The composition can also be provided in the form of an aqueous solution, preferably a hydroalcoholic solution, or a glycerin-alcoholic solution or even a glycerine hydroalcoholic solution. In these alcohol containing solutions, the alcohol is preferably ethanol or isopropanol and it is present in an amount between 10 and 90 weight percent, preferably between 40 and 60 weight percent relative to the total weight of the composition. The glycerine, when present, is employed preferably in an amount between 0.5 and 5 weight percent, more preferably in an amount of 2 weight percent based on the total weight of the composition. This cosmetic composition can also contain a wetting agent including oxyethylenated derivatives such as lanolin ethoxylated with 25 moles of ethylene oxide or polyethylene glycol.

The composition, in lotion form, can also be an oleoalcohol composition containing preferably a vegetable oil such as for example colza oil, olive oil, peanut oil, coconut oil and palm oil; a lower alkyl ester such as isopropyl myristate or isopropyl palmitate; and a lower alcohol having preferably 1-4 carbon atoms and more particularly ethanol. The vegetable oil is present preferably in an amount of 0.2 to 5 weight percent, the alkyl ester, in an amount of 5 to 40 weight percent; and the alcohol in an amount of 35–80, preferably 40 to 75 weight percent, based on the total weight of the composition. In this oleo-alcohol form of the composition, the concentration of the quinoxaline derivative of formula (I) is preferably between 0.5 and 3 weight percent due to its reduced solubility in this oleo-alcohol carrier or vehicle.

The composition of the present invention can also be packaged under pressure in an aerosol container together with a gaseous propellant selected from nitrogen, nitrous oxide, a volatile hydrocarbon such as butane, isobutane or propane or, preferably, a fluorinated hydrocarbon sold under the name of Freon and in particular such fluorocarbons as dichlorodifluoromethane (Freon 12), dichlorotetrafluoromethane (Freon 114) and trichloromonofluoromethane (Freon 11). These propellants can be used singly or in combination.

When the composition of this invention is in the form of an aqueous gel, it includes, generally, a surfactant selected from a fatty alcohol having 12–18 carbon atoms and oxyethylenated with 4–15 and preferably with 6–12 moles of ethylene oxide; nonylphenol oxyethylenated with 6–12 moles of ethylene oxide; a carboxylic derivative of imidazole; and a gel forming agent selected from a cellulose ether, carboxy methyl cellulose or a crosslinked polyacrylic acid sold under the trade name Carbopol.

The aqueous gel can also include a silicone oil, which when it is present, is emulsified by the surfactant.

The surfactant is present preferably in an amount from 1 to 25 and, preferably, from 1 to 10 weight percent; the gel forming agent in an amount from 0.5 to 4, and preferably from 1 to 2.5 weight percent; and the silicone oil, in an amount up to 2 weight percent, and preferably 0.1 weight percent, based on the total weight of the composition.

In a particularly preferred embodiment of the invention, the composition is provided in the form of an oil-in-water emulsion. This emulsion contains a surfactant, an oil, a thickening agent and a humectant. The surfactant which is present, preferably, in an amount from 2 to 20, and more preferably, from 10 to 16 weight percent is selected from such emulsifying agents as a fatty alcohol having 12–18 carbon atoms and oxyethylenated with 10–15 moles of ethylene oxide; isopropyl palmitate, isopropyl myristate; glycerol monostearate; polyoxyethylenated sorbitan monostearate; a self-emulsifying wax selected from partially sulfated or partially oxyethylenated cetyl stearyl alcohols; and a mixture of these emulsifying agents or waxes. The oil or fatty phase of this emulsion is present in an amount between 10 and 50 weight percent and can be a light petrolatum oil; perhydrosqualene; a vegetable oil such as sweet almond oil, ricin oil, colza oil, olive oil, peanut oil, coconut oil and palm oil; a fatty alcohol having for example 7 carbon atoms; and a saturated fatty acid having, for example, 18 carbon atoms. The thickening agent employed in this emulsion is present in an amount between 0 and 6 weight percent and can be, for instance, starch, a crosslinked polyacrylic acid sold under the mark Carbopol or diethylene glycol stearate. The humectant in the emulsion is preferably glycerine and is present in an amount of 0 to 15 weight percent.

When the surfactant employed in this emulsion is a partially sulfated or partially oxyethylenated cetyl-stearyl alcohol, the non-oxyethylenated or non-sulfated portion thereof serves as the oil or fatty phase in this oil-in-water emulsion.

This oil-in-water emulsion can be provided as a milk or a cream, but it can also be packaged under pressure in an aerosol container together with an aerosol propellant such as defined above.

The composition of the present invention can also contain various other components or adjuvants conventionally employed in cosmetic preparations of this type. Representative adjuvants include principally perfumes, preservatives, softening agents, super-fatting agents, emollients, antifoam agents and the like.

The pH of the composition of the present invention can be adjusted by the addition thereto of an acid such as acetic acid or citric acid, or a base, such as monoethanolamine or triethanolamine.

The composition according to the present invention can also contain a solar filter so as to protect the skin against harmful radiations. The inclusion of a filter also permits over a period of time to modulate the deepening of the color as a function of the amount of solar filter in the composition, as well as the nature of the said solar filter.

Representative solar filters usefully employed in the present invention include such known materials as the following salicylic acid derivatives: amyl, phenyl, benzyl, methyl, glyceryl, dipropylene glycol and in particular 2-ethyl hexyl, 3,3,5-trimethyl hexyl, 2-phenyl, sodium, triethanolamine and benzyl methyl eugenol salicylates;

the following cinnamic acid derivatives: methyl and benzyl esters, α-phenyl cinnamo nitrile, butyl cinnamoyl pyruvate; dihydroxy cinnamic acid derivatives such as umbelliferone, methyl umbelliferone, methyl aceto-umbelliferone; tri-hydroxy cinnamic acid derivatives such as esculetine, methyl esculetine, daphnetine and esculine and daphnine glucosides; the cinnamic acid derivatives more particularly preferred are 2-ethoxy ethyl paramethoxy cinnamate, isobutyl salicyl cinnamate, ethyl paramethoxy cinnamate, cyclohexyl para-methoxy cinnamate, ethyl hexyl para-methoxy cinnamate, the esters of substituted cinnamic acid and the potassium salt of methoxy cinnamic acid;

the following para-amino benzoic acid derivatives: ethyl, isobutyl and glyceryl esters of p-amino benzoic acid; 4-amino benzoic acid polyoxyethylenated with 25 moles of ethylene oxide, the monoglyceryl ester of paraamino benzoic acid, oxyethylenated derivatives of paraamino benzoic acid, amyl paradimethyl benzoate, butyl para dimethyl amino benzoate, ethyl para dimethylamino benzoate, methyl para dimethyl amino benzoate and ethyl para diethylamino benzoate;

the following benzophenone derivatives: substituted benzophenone sold under the commercial names "UVINOL 410" and "UVINUL 490", 2,4-dihydroxy benzophenone, 2,2'-dihydroxy 4-methoxy benzophenone, 2,2'-dihydroxy-4,4'-dimethoxy benzophenone, 2-hydroxy-4-N-ethoxy benzophenone, 2-hydroxy-4-methoxy benzophenone, 2-hydroxy-4-methoxy benzophenone-5-sulphonic acid and its sodium salt, 2-hydroxy-4-methoxy-4'-methyl benzophenone, 2-hydroxy-5-chloro benzophenone 2'-isooctyl carboxylic acid ester, 2,2'-dihydroxy-4,4'-dimethoxy benzophenone 5-sulphonic acid and its sodium salt, and 2,2',4,4'-tetrahydroxy benzophenone;

the following coumarin derivatives: hydroxy coumarin, dihydroxy coumarin and 7-diethylamino-4-methyl coumarin;

the following azoles: benzotriazole derivatives such as 5'-methyl-2'-hydroxy phenyl benzotriazole and 2,2'-dihydroxy3',5'-ditertio butyl phenyl-5-chloro benzotriazole;

the following imidazole derivatives: imidazole 4-acrylic acid, 2-phenyl benzimidazole-5-sulfonic acid, 2-acetyl-3-bromoindazole, phenyl benzoxazole, methyl naphtoxazole and various arylbenzothiazoles;

the following naphtosulfonates: the sodium salts of 2-naphtol 3,6-disulfonic acid and naphtol 6,8-disulfonic acid;

the following quinine salts: the disulfate, the sulfate, the chloride, the oleate, the tannate; the quinolein derivating including the salts of 8-hydroxy quinolein or the salts of 2-phenyl quinolein, tannic acid and its derivatives such as the hexaethylether thereof;

acetanilide, benzalhydrazine and dibenzalhydrazine;

hydroquinone and its derivatives such as 2,4-dibenzoyl resorcinol, unsaturated cyclic ketone, aromatic esters of higher aliphatic alcohol, sesame oil, sodium 3,4-dimethoxy phenyl glyoxylate, digaloyl trioleate, benzoyl phenyl carbinol, benzylidene camphor and its derivatives, 2-phenyl indol and its derivatives.

Among these solar filters, the last two types are described more fully in French Pat. Nos. 7334140, 7405427, 7428478 and 7526732.

These solar filters are used in an amount between 0.5 and 5 and preferably between 1 and 3 weight percent relative to the total weight of the composition.

The more particularly preferred solar filters include benzylidene camphor, ethyl hexyl para methoxy cinnamate, amyl para dimethylamino benzoate, benzophenone derivatives such as 5-benzoyl-4-hydroxy-2-methoxy benzene sulfonic acid, hydroxy propylenated derivatives of ethyl p-amino benzoate and the diethanolamine salt of p-methoxy cinnamic acid.

The cosmetic composition of this invention is stored out of contact with light and is perfectly stable.

The process of coloring the skin in accordance with the present invention comprises applying to the skin the composition defined above using any procedure so as to obtain a uniform distribution of the composition on the skin, and exposing the thus treated skin to light rays having a wave length of 320 to 400 millimicrons. After a period of time which is clearly shorter than would be necessary to obtain a natural tan, a skin coloration, essentially comparable to the said natural tan is obtained. This process also makes it possible to modulate, over a period of time, the appearance of this coloration by the addition to the composition of a solar filter as defined above. The appearance of the coloration if it is delayed by the inclusion of a solar filter is nonetheless effected quite rapidly relative to the exposure time required to obtain a natural tan and without producing a sunburn.

The quinoxaline derivatives employed in the composition of the present invention are known and can be prepared in accordance with procedures described in the literature, including the reaction of benzofuroxan with a ketonic derivative or an enaminated compound, or by condensation of an orthophenylene diamine with a di-ketonic compound.

The quinoxaline derivatives employed in the present invention can be prepared principally by any one of the three following procedures:

Method A 0.1 mole of benzofuroxan is suspended in 500 cc of methanol. To this suspension there is added 0.1 mole of a ketone compound, after which there is slowly introduced 0.1 mole of butylamine. The benzofuroxan progressively goes into solution. The reaction mixture is agitated for 5 hours at 30° C., is then filtered and the resulting quinoxaline di-N-oxide derivative is dried and then recrystallized in an appropriate solvent.

Method B 0.1 mole of benzofuroxan is dissolved, with heat, in 400 cc of methanol. To this solution there is slowly added 0.1 mole of an enaminated compound and the resulting mixture is agitated for an hour and then filtered. The resulting quinoxaline di-N-oxide is recrystallized in an appropriate solvent.

Method C

The desired quinoxaline derivative is prepared by condensation of an orthophenylene with an α-diketonic compound or its bisulfitic combination in accordance with the procedures described in Org. Synthese Coll. IV., p. 824.

0.1 mole of the resulting quinoxaline is dissolved in 260 cc of peracetic acid (1.2 mole) and the solution is heated overnight at 50° C. The excess acid is distilled off under reduced pressure and the residue is poured over 150 g of ice. The reaction mixture is the neutralized by the addition thereto of 40% NaOH. The precipitate which forms is then filtered and washed with distilled water.

The following non-limiting examples are given to illustrate the invention. Unless otherwise specified, all parts and percentages are by weight.

EXAMPLE 1

Nonionic-based Emulsion

Nonionic emulsions are prepared and contain:

(a) 10–18% of an emulsifying agent comprising Sipol wax (mixture of stearyl alcohol and oleo-cetyl alcohol oxyethylenated with 25 moles of ethylene oxide), glycerol monostearate and cetyl alcohol;

(b) 10–20% of an oil comprising a silicone oil, sold under the mark RHODORSIL 47V300, which is a dimethylpolysiloxane having a viscosity of 300 cp at 25° C., a flash point of 320° C., a density at 20° C. of 0.95–0.97, and petrolatum oil-Codex;

(c) 1–20 percent of a humectant comprising glycerine;

(d) 0–1% perfume;

(e) 1–5% of the quinoxaline derivative of formula (I); and (f) water, sufficient for 100%.

The pH of this composition is between 5 and 6 and is stored in a bottle out of contact with light.

This composition is applied to the skin or onto an inert support using conventional spreading means.

This procedure imparts to the skin a coloration resembling a natural tan after an exposure to light rays as defined above, for a period ranging from 5 to 30 minutes. In order to provide a more objective evaluation of the results, which are not influenced by the nature or the initial appearance of the human skin, or by the solar illumination which can be variable, most of the following tests have been carried out using an inert support.

A specific composition of this invention in the form of an oil-in-water emulsion is prepared by admixing the following components:

Sipol wax (mixture of stearyl alcohol and oleo-cetyl alcohol oxyethylenated with 25 moles of ethylene oxide): 7 g
Glycerol monostearate: 2 g
Cetyl alcohol: 1.5 g
Silicone oil (sold under the mark RHODORSIL 47V300): 1.5 g
Petrolatum oil-CODEX: 15 g
Glycerine: 10 g
Perfume (sold under the mark CREMATEST 094990): 0.5 g
2-methyl quinoxaline di-N-oxide: 3 g
Water, sufficient for: 100 g This composition which had been stored out of contact with light for several days was applied to the skin. After exposure of the thus treated skin to the bright midday sun for a period of 10–20 minutes, a coloration similar to a natural tan developed on the skin.

The application of this same composition to an inert support comprising a glass plate, also provided after an exposure of about 10–20 minutes to ultra-violet rays a brown coloration resembling that of a natural tan.

Using essentially the same composition but replacing a portion of the petrolatum oil-CODEX with 1.5 g of benzylidene camphor, there resulted on the inert support a deepening of the color identical to that previously obtained, at the end of 10 to 20 minutes.

By replacing the 2-methyl quinoxaline di-N-oxide with another photo-dye responding to formula I, results set forth in Table I were achieved. These tests have been carried out as mentioned above on an inert support to provide a more objective reference. However, the color developed on the inert support is essentially the same natural tan coloration achieved when the same composition is applied to human skin.

Similar results are obtained by varying the amount of the different components of the composition within said ranges specified above.

The pH of these compositions varies with the photo-dye added. The pH is, for example, equal to 4.3 for the composition of the type defined below containing 5 weight percent 3-methyl quinoxaline di-N-oxide and 2.5 weight percent benzylidene camphor, and 5.9 for the composition containing 5 g of 2,3-dimethyl quinoxaline di-N-oxide and 2.5 g of benzylidene camphor.

EXAMPLE 2

Anionic-based Emulsion

Anionic-based emulsions are prepared and contain:

(a) 10–16% of an emulsifying agent comprising self-emulsifiable glycerine monostearate (sold under the mark ARLACEL 165), sorbitan monostearate polyoxyethylenated with 60 moles of ethylene oxide (sold under the mark TWEEN 60), pure stearic acid (triple pressure) and cetyl alcohol;

(b) 35-50% of an oil comprising petrolatum oil-CODEX;
(c) 0-1% triethanolamine;
(d) 0-1% perfume;
(e) 1-5% of the quinoxaline derivative of formula (I); and
(f) water, sufficient for 100%.

The pH of these compositions is adjusted to 7.

As in Example 1, the anionic-based emulsion is applied to the skin or onto the same inert support. As before, at the end of a period ranging from 10 minutes to 20 minutes, the appearance of a coloration essentially the same as that obtained using the same compound in Example 1 is achieved.

Using an emulsion having the following composition:

Self-emulsifiable glycerine monostearate (sold under the mark ARLACEL 165): 6 g
Sorbitan monostearate polyoxyethylenated with 60 moles of ethylene oxide (sold under the mark TWEEN 60): 2 g
stearic acid, pure, triple pressure: 2 g
Cetyl alcohol: 1.2 g
Petrolatum oil-CODEX: 38.5 g
Triethanolamine: 0.1 g
Perfume (sold under the mark No. 959/2): 0.5 g
2,3-dimethyl quinoxaline di-N-oxide: 3 g
Water, sufficient for: 100 g A brown coloration, on normal skin after a 20 minute exposure to the bright midday sun is achieved, this coloration being essentially the same as a natural tan.

The use of a solar filter and/or another quinoxaline derivative of formula (I) in various other compositions provides those results set forth in Table II. The tests leading to these results have been carried out, as before, on an inert support.

Similar results are obtained by varying the amount and nature of the different components in these compositions.

EXAMPLE 3

Lotions

A composition of the present invention in lotion form is prepared and contains:

(a) 0.5-2% of lanolin ethoxylated with 25 moles of ethylene oxide;
(b) 0.5-5% of polyethylene glycol (M.W=400);
(c) 1-10% of sorbitol (70%);
(d) 40-60% ethyl alcohol (96°);
(e) 0-1% of perfume;
(f) 1-5% of the quinoxaline derivative of formula (I); and
(g) water, sufficient for 100%.

This lotion is applied to the skin, for example, by spraying and provides after exposure to the sun for a period between 10 and 20 minutes, a coloration essentially the same as a natural tan.

Using a lotion having the following composition:

Lanolin, ethoxylated with 25 moles of ethylene oxide: 1 g
Polyethylene glycol (M.W.=400): 1 g
Sorbitol (70% in water): 5 g
Ethyl alcohol, 96° titer: 50 g
Perfume (Robertet LT 13.999): 0.5 g
2-methyl-2-phenyl quinoxaline di-N-oxide: 3 g
Water, sufficient for: 100 g A coloration resembling a natural tan is achieved after an exposure of 20 minutes to a bright midday sun.

The inclusion of ethyl hexyl p-methoxy cinnamate in an amount of 1.5% based on the ethyl alcohol, provides after an exposure of 30 minutes to the sun a tan coloration essentially the same as that obtained above.

By replacing the photo-dye and/or filter by the components listed in Table III, the results shown therein are achieved. These tests, as before, have been made using an inert support.

Amerscreen P is the mark for a product comprising ethyl monohydroxy propylamino benzoate and ethyl di-hydroxy propyl amino benzoate in a ratio of 1:3, which has a molecular weight of 281.

TABLE I

| Nonionic Emulsion | | | | | |
|---|---|---|---|---|---|
| Photo-dye | | Filter | | Time of | |
| Nature | Amount wt % | Nature | Amount wt % | Exposure (min) | Coloration Achieved |
| 3-methyl quinoxaline di-N-oxide | 2.5 | | | 20 | yellow chestnut |
| 3-methyl quinoxaline di-N-oxide | 5 | | | 15 | yellow chestnut |
| 3-methyl quinoxaline di-N-oxide | 5 | benzylidene camphor | 2.5 | 30 | yellow chestnut |
| 3-methyl quinoxaline di-N-oxide | 2.5 | amyl p-dimethylamino benzoate | 3 | 30 | yellow chestnut |
| 3-methyl quinoxaline di-N-oxide | 2.5 | ethyl hexyl p-methoxycinnamate | 1.5 | 30 | yellow chestnut |
| 2,3-dimethyl quinoxaline di-N-oxide | 2.5 | | | 15 | caramel brown |
| 2,3-dimethyl quinoxaline di-N-oxide | 5 | | | 10 | caramel brown |
| 2,3-dimethyl quinoxaline di-N-oxide | 5 | benzylidene camphor | 2.5 | 25 | brown |
| 2,3-dimethyl quinoxaline di-N-oxide | 2.5 | amyl p-dimethyl amino benzoate | 3 | 30 | chestnut brown |
| 2,3-dimethyl quinoxaline di-N-oxide | 2.5 | ethyl hexyl p-methoxy cinnamate | 1.5 | 30 | brown |
| 3-methyl quinoxaline di-N-oxide and 2,3-dimethyl quinoxaline di-N-oxide | 2.5<br>2.5 | | | 15 | brown ocher |

TABLE I-continued

| Photo-dye | | Nonionic Emulsion Filter | | Time of | |
|---|---|---|---|---|---|
| Nature | Amount wt % | Nature | Amount wt % | Exposure (min) | Coloration Achieved |
| 2-ethyl-3-methyl quinoxaline di-N-oxide | 2.5 | | | 15 | deep brown ocher |
| 2-ethyl-3-methyl quinoxaline di-N-oxide | 5 | | | 10 | deep brown ocher |
| 2-ethyl-3-methyl quinoxaline di-N-oxide | 2.5 | amyl p-dimethyl amino benzoate | 3 | 30 | red brown |
| 2-ethyl-3-methyl quinoxaline di-N-oxide | 2.5 | ethyl hexyl p-methoxy cinnamate | 1.5 | 30 | red brown |
| 2-ethyl-3-methyl quinoxaline di-N-oxide | 2.5 | 5-benzoyl-4-hydroxy-2-methoxy-benzene sulfonic acid | 3 | 35 | brown |
| 2,3-propylene quinoxaline di-N-oxide | 2.5 | | | 20 | green brown |
| 2,3-propylene quinoxaline di-N-oxide | 2.5 | amyl p-dimethyl amino benzoate | 3 | 30 | green brown |
| 2,3-propylene quinoxaline di-N-oxide | 2.5 | ethyl hexyl p-methoxy cinnamate | 1.5 | 30 | green brown |

TABLE II

| Photo-dye | | Anionic Emulsion Filter | | Time of | |
|---|---|---|---|---|---|
| Nature | Amount wt % | Nature | Amount wt % | Exposure (min) | Coloration Achieved |
| 3-methyl quinoxaline di-N-oxide | 2.5 | | | 20 | yellow brown |
| 3-methyl quinoxaline di-N-oxide | 5 | | | 15 | yellow brown |
| 3-methyl quinoxaline di-N-oxide | 5 | benzylidene camphor | 2.5 | 30 | deep yellow |
| 3-methyl quinoxaline di-N-oxide | 2.5 | ethyl hexyl p-methoxy cinnamate | 1.5 | 30 | deep yellow |
| 3-methyl quinoxaline di-N-oxide | 2.5 | amyl p-dimethyl amino benzoate | 3 | 30 | deep yellow |
| 2,3-dimethyl quinoxaline di-N-oxide | 2.5 | | | 15 | red brown |
| 2,3-dimethyl quinoxaline di-N-oxide | 5 | | | 10 | red brown |
| 2,3-dimethyl quinoxaline di-N-oxide | 5 | benzylidene camphor | 2.5 | 25 | brown ocher |
| 2,3-dimethyl quinoxaline di-N-oxide | 2.5 | amyl p-dimethyl amino benzoate | 3 | 30 | yellow brown |
| 2,3-dimethyl quinoxaline di-N-oxide | 2.5 | ethyl hexyl p-methoxy cinnamate | 1.5 | 30 | yellow brown |
| 2-ethyl-3-methyl quinoxaline di-N-oxide | 2.5 | | | 20 | red brown |
| 2-ethyl-3-methyl quinoxaline di-N-oxide | 2.5 | ethyl hexyl p-methoxy cinnamate | 1.5 | 35 | orange brown |
| 2-ethyl-3-methyl quinoxaline di-N-oxide | 2.5 | amyl p-dimethyl amino benzoate | 3 | 30 | orange brown |
| 2-ethyl-3-methyl quinoxaline di-N-oxide | 2.5 | 5-benzoyl-4-hydroxy-2-methoxy benzene sulfonic acid | 3 | 30 | brown |
| 2,3-propylene quinoxaline di-N-oxide | 2.5 | | | 20 | greenish brown |
| 2,3-propylene quinoxaline di-N-oxide | 2.5 | 5-benzoyl-4-hydroxy-2-methoxy benzene sulfonic acid | 3 | 30 | greenish |
| 2,3-propylene quinoxaline di-N-oxide | 2.5 | amyl p-dimethyl amino benzoate | 3 | 30 | green brown |
| 2,3-propylene quinoxaline di-N-oxide | 2.5 | ethyl hexyl p-methoxy cinnamate | 1.5 | 30 | green brown |

TABLE III

| Photo-dye | | Hydroalcoholic Lotion Filter | | Time of | |
|---|---|---|---|---|---|
| Nature | Amount wt % | Nature | Amount wt % | Exposure (Min) | Coloration Achieved |
| 3-methyl quinoxaline di-N-oxide | 5 | | | 10 | yellow ocher |
| 3-methyl quinoxaline di-N-oxide | 5 | 5-benzoyl-4-hydroxy-2-methoxy | | | |

TABLE III-continued

| Hydroalcoholic Lotion | | | | | | |
|---|---|---|---|---|---|---|
| Photo-dye | | Filter | | Time of | | |
| Nature | Amount wt % | Nature | Amount wt % | Exposure (Min) | Coloration Achieved |
| | | benzene sulfonic acid | 1.5 | 15 | yellow |
| 2,3-dimethyl quinoxaline di-N-oxide | 2.5 | | | 15 | caramel brown |
| 2,3-dimethyl quinoxaline di-N-oxide | 5 | | | 10 | caramel brown |
| 2,3-dimethyl quinoxaline di-N-oxide | 2.5 | 5-benzoyl-4-hydroxy-2-methoxy benzene sulfonic acid | 1.5 | 20 | caramel brown |
| 2,3-dimethyl quinoxaline di-N-oxide | 5 | 5-benzoyl-4-hydroxy-2-methoxy benzene sulfonic acid | 3 | 18 | caramel brown |
| 2-ethyl-3-methyl quinoxaline di-N-oxide | 5 | | | 15 | deep brown ocher |
| 2-ethyl-3-methyl quinoxaline di-N-oxide | 5 | AMERSCREEN P | 1.5 | 25 | red brown |
| 2,3-propylene quinoxaline di-N-oxide | 5 | | | 15 | gray-green brown |
| 2,3-propylene quinoxaline di-N-oxide | 5 | diethanolamine salt of p-methoxy cinnamic acid | 1.5 | 25 | green brown |

What is claimed is:

1. A process for coloring human skin comprising applying to the skin in an amount sufficient to impart to said skin after exposure to ultraviolet rays a coloration resembling a natural tan a composition comprising a cosmetic vehicle suitable for topical application to the skin selected from the group consisting of (1) a hydroalcoholic solution containing 10–90 weight percent alcohol, (2) a glycerin-alcoholic solution containing 10–90 weight percent alcohol, (3) a glycerin-hydroalcoholic solution containing 10–90 weight percent alcohol, (4) an oleo-alcohol composition containing a vegetable oil, a lower alkyl ester and a lower alcohol having 1–4 carbon atoms, (5) an aqueous gel including a surfactant and a gel forming agent, and (6) an oil-in-water emulsion including a surfactant, an oil, a thickening agent and a humectant, and at least one compound selected from the group consisting of (a) a compound of the formula

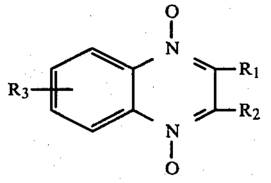

wherein $R_1$ and $R_2$ each independently represent hydrogen, a linear or branched alkyl having 1–18 carbon atoms, carbalkoxy having 2–5 carbon atoms, acyl having 2–5 carbon atoms, phenyl and phenyl substituted by a member selected from the group consisting of alkyl having 1–4 carbon atoms and hydroxy, and $R_3$ represents hydrogen, lower alkyl containing 1–6 carbon atoms, lower alkoxy containing 1–4 carbon atoms or halogen, with the proviso that $R_1$, $R_2$ and $R_3$ are not hydrogen simultaneously; and (b) an acid addition salt of the compound in (a), said compound being present in an amount of 0.5–10 percent by weight of said composition, and said composition having a pH between 3 and 8.5, and exposing the skin to ultraviolet rays for a time effective to develop said color on said skin.

2. The process of claim 1, wherein said compound is selected from the group consisting of:
3-methyl quinoxaline di-N-oxide,
2,3-dimethyl quinoxaline di-N-oxide,
2-methyl-3-phenyl quinoxaline di-N-oxide,
2-methyl-3-p-hydroxyphenyl quinoxaline di-N-oxide,
2-ethyl-3-methyl quinoxaline di-N-oxide,
2-isopropyl-3-methyl quinoxaline di-N-oxide,
2-decyl-3-methyl-quinoxaline di-N-oxide,
2-hexadecyl-3-methyl quinoxaline di-N-oxide,
2-carbethoxy-3-methyl quinoxaline di-N-oxide,
2-acetyl-3-methyl quinoxaline di-N-oxide,
2,3-dimethyl-6-methoxy quinoxaline di-N-oxide,
2,3-dimethyl-6-chloro quinoxaline di-N-oxide,
2-ethyl-3,6-dimethyl quinoxaline di-N-oxide,
and the acid addition salts thereof.

3. The process of claim 1, wherein said acid addition salt is a hydrochloride, a sulfate, an acetate, a tartrate, a perchlorate, a citrate or a stearate.

4. The process of claim 1 wherein said composition also includes a solar filter in an amount of 0.5–5 percent by weight thereof.

5. The process of claim 4 wherein said solar filter is selected from the group consisting of benzylidene camphor, ethyl hexyl p-methoxy cinnamate, amyl p-dimethylamino benzoate, 5-benzoyl-4-hydroxy-2-methoxy benzene sulfonic acid, hydroxypropylenated derivative of a p-amino benzoate and the diethanolamine salt of p-methoxy cinnamic acid.

6. The process of claim 1 wherein said cosmetic vehicle is (4) and wherein said vegetable oil is present in an amount of 5–40 weight percent, the alcohol is present in an amount of 35–80 weight percent and the alkyl ester is present in an amount of 5–40 weight percent.

7. The process of claim 1 where, in the said composition, the said cosmetic vehicle is (5) and wherein said surfactant is present in an amount of 1–25 weight percent and said gel forming agent is present in an amount of 0.5–4 weight percent.

8. The process of claim 7 wherein the composition also includes a silicone oil in an amount up to about two weight percent.

9. The process of claim 1 wherein, in the said composition, the said cosmetic vehicle is (6) and wherein said surfactant is present in an amount of 2–20 weight percent, said oil is present in an amount of 10–50 weight percent, said thickening agent is present in an amount of 0–6 weight percent and said humectant is present in an amount of 0–15 weight percent.

10. The process of claim 6 wherein said vegetable oil is colza oil, olive oil, peanut oil, coconut oil or palm oil.

11. The process of claim 6 wherein said alkyl ester is isopropyl myristate or isopropyl palmitate.

12. The process of claim 6 wherein said alcohol is ethanol.

13. The process of claim 7 wherein said surfactant is a fatty alcohol having 12–18 carbon atoms oxyethylenated with 4–15 moles of ethylene oxide, nonylphenol oxyethylenated with 6–12 moles of ethylene oxide or a carboxylic derivative of imidazole.

14. The process of claim 7 wherein said gel forming agent is cellulose ether, carboxy methyl cellulose or crosslinked polyacrylic acid.

15. The process of claim 9 wherein said surfactant is a fatty alcohol having 12–18 carbon atoms oxyethylenated with 10–15 moles of ethylene oxide, isopropyl palmitate, isopropyl myristate, glycerol monostearate, polyoxyethylenated sorbitan monostearate, partially sulfated or partially oxyethylenated cetyl-stearyl alcohol, or a mixture thereof.

16. The process of claim 9 wherein said oil is light petrolatum oil, perhydrosqualene, sweet almond oil, ricin oil, colza oil, olive oil, peanut oil, coconut oil, palm oil, fatty alcohol having 7 carbon atoms or a saturated fatty acid having 18 carbon atoms.

17. The process of claim 9 wherein said thickening agent is starch, crosslinked polyacrylic acid or diethylene glycol stearate.

18. The process of claim 9 wherein said humectant is glycerin.

19. The process of claim 1 wherein said compound is 2,3-dimethyl quinoxaline di-N-oxide.

* * * * *